United States Patent [19]
Sawyer

[11] Patent Number: 5,992,996
[45] Date of Patent: Nov. 30, 1999

[54] PROTECTIVE EYEWEAR INCLUDING AN INTEGRAL THERMOLUMINESCENT DOSIMETRY CHIP FOR MEASURING FACIAL EXPOSURE TO IONIZING RADIATION

[76] Inventor: Robert N. Sawyer, 149 Prospect Ave., Guilford, Conn. 06437

[21] Appl. No.: 09/131,901
[22] Filed: Aug. 10, 1998
[51] Int. Cl.⁶ .................................................... G02C 1/00
[52] U.S. Cl. ............................................. 351/158; 351/41
[58] Field of Search ................................. 351/41, 158, 44

[56] References Cited

U.S. PATENT DOCUMENTS

| | | |
|---|---|---|
| 2,855,519 | 10/1958 | Kocher . |
| 3,597,054 | 8/1971 | Winter . |
| 3,657,538 | 4/1972 | Fergason et al. . |
| 3,878,108 | 4/1975 | Burgkhard . |
| 4,372,680 | 2/1983 | Adams et al. . |
| 5,151,600 | 9/1992 | Black . |
| 5,446,507 | 8/1995 | Chang . |

*Primary Examiner*—Hung Xuan Dang
*Attorney, Agent, or Firm*—McCormick, Paulding & Huber LLP

[57] ABSTRACT

In an apparatus for measuring facial exposure to radiation, a housing is provided and includes a first recess defined in-part by an end wall. A chip holder is also provided and defines a second recess adapted to carry a thermoluminescent dosimetry chip. The chip holder is positioned in the first recess with the end wall and the first recess cooperating to form a chamber that encapsulates the thermoluminescent dosimetry chip. The apparatus is mountable to an eye protective device, such as a face shield, eyeglasses, or safety glasses to measure the amount of radiation to which the facial area of the wearer is exposed.

9 Claims, 2 Drawing Sheets

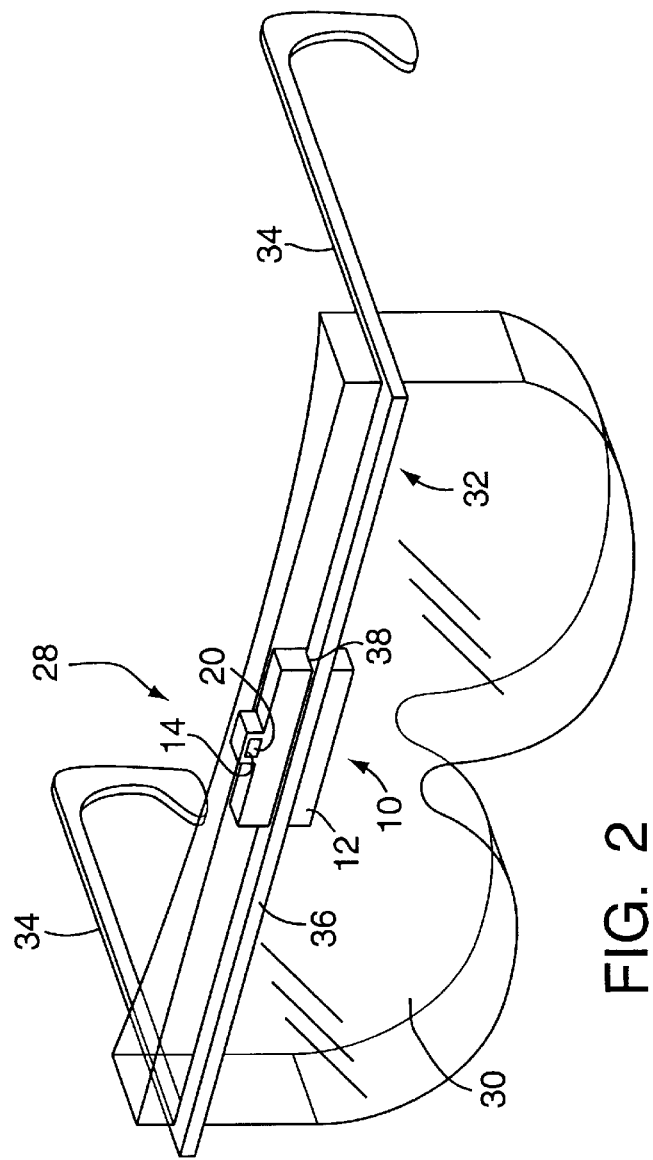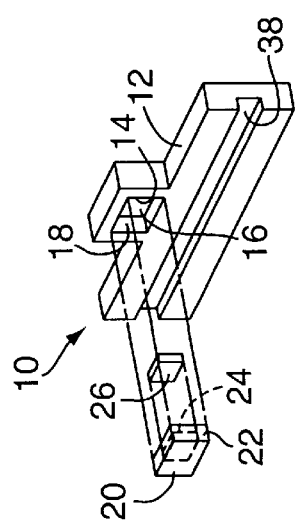

PROTECTIVE EYEWEAR INCLUDING AN INTEGRAL THERMOLUMINESCENT DOSIMETRY CHIP FOR MEASURING FACIAL EXPOSURE TO IONIZING RADIATION

FIELD OF THE INVENTION

The present invention is directed generally to dosimeters for measuring cumulative exposure to radiation, and deals more particularly with a dosimeter that can be mounted to an eye protective device, such as a face shield, eye glasses, safety glasses, or similar protective apparatus, to measure the cumulative exposure to radiation of the eyes and facial area of an individual wearing the protective device.

BACKGROUND OF THE PRESENT INVENTION

Ionizing radiation creates a risk of injury to persons exposed to such energy. Such radiation can be natural or generated and numerous sources can be encountered in medicine industry, research and academic work. As an example, ionizing radiation is often generated by various types of equipment, such as x-ray machinery, used in the medical or dental profession. Accordingly, there is a heightened risk of exposure to persons who work in this discipline. To avoid prolonged, or over-exposure to radiation, as well as to comply with federal regulations, the exposure to radiation of involved medical professionals is generally closely monitored.

Two groups of devices are most commonly used to measure exposure to radiation. The first type of device consists of a meter that detects and quantifies the level or intensity of radioactivity. These devices make instantaneous measurements and do not typically provide information regarding accumulation of exposure. The second group of devices measures the accumulated amount of radiation a person has been exposed to over a given period of time, and are referred to by those skilled in the pertinent art as dosimeters.

Dosimeters provide information on accumulated radiation exposure by integrating the various different, and often variable intensity doses of radiation to which a person is exposed over a given period of time. The duration of data collection can vary from minutes to weeks depending on exposure conditions and surveillance requirements. Usually, the dosimeter is in the form of a badge that can be clipped onto a person's clothing.

Dosimeters can include real time devices, i.e., the self reading gauge dosimeters (SRD); and those requiring processing: film radiation detectors; and thermoluminescent dosimetry (TLD), utilizing lithium fluoride (LiF) chips. The TLD is the most robust, reliable and accurate means of dose estimation.

Usually, a dosimeter is worn in proximity to the chest or waist, and is clipped onto clothing or suspended from a chain. Dosimeters can also be attached to the extremities or other locations on the body to provide more accurate data appropriate to a specific exposure situation. However, difficulties sometimes arise as a result of a person forgetting to attach the dosimeter, or as a result of inappropriate placement of the dosimeter when localized exposure occurs. This can result in undetected overexposure, that in turn could injure the unsuspecting individual. This problem is most frequently encountered when a person's face and eyes are exposed to a discrete beam of radiation, and the dosimeter is positioned below the person's neck.

Based on the foregoing, it is the general object of the present invention to provide a radiation measurement device that overcomes the problems and drawbacks associated with prior art devices.

It is a more specific object of the present invention to provide a device capable of accurately measuring the level of exposure to radiation of the facial area of an individual.

SUMMARY OF THE PRESENT INVENTION

The present invention is directed to an apparatus for measuring facial exposure to ionizing radiation, mountable on an eye protective device. As used herein, the phrase "eye protective device" should be broadly construed to include eyeglasses, safety glasses, goggles, face shields and like devices. In the preferred embodiment of the present invention, the apparatus includes a housing having a first recess defined in-part by an end wall. A plug is also included and has an outer periphery of a shape complimentary to the first recess, thereby allowing the plug to be slidably received, and frictionally retained in the first recess. The recess and plug thus define a space adapted to receive and releasably retain a thermoluminescent dosimetry chip.

When the plug is positioned in the first recess defined by the housing, the end wall acts as a closure for the chip space, thereby defining a chamber that encapsulates and protects the thermoluminescent dosimetry chip. Means are also provided for releasably coupling the housing to an upper brow portion of the eye protective device, such that the thermoluminescent dosimetry chip can measure the amount of radiation to which the face and eyes of the wearer are exposed.

In one embodiment of the present invention, the eye protective device includes a frame having a bridge portion that has an opening extending there-through defined by an inner perimeter. The housing defines an outer perimeter of a shape complimentary to the inner perimeter in the brow portion of the frame. Accordingly, when the housing is positioned in the bridge opening, the second perimeter slidably engages the first perimeter and is frictionally retained therein.

In another embodiment of the present invention, the eye protective device comprises a pair of safety glasses having a frame coupled to at least one lens member. The frame includes a pair of ear pieces and an elongated brow member interposed between and coupled to the ear pieces, and extending across an upper portion of the lens member. In this embodiment, it is preferable that the above-described means for releasably coupling the housing to an upper brow portion of the eye protective device includes a longitudinal slot defined by and extending part-way through the housing. The slot is adapted to receive a portion of the elongated brow member when the housing is positioned between and frictionally held in place by the brow and lens members.

In all of the above-described embodiments, it is preferable that the housing and the plug be made from a suitable material such as high density polypropylene. It is also preferable that the thermoluminescent dosimetry chip be a lithium fluoride chip.

In yet another embodiment of the present invention, a pair of safety glasses comprises a frame that includes an upper brow area defining a recess adapted to frictionally and releasably retain the plug. The recess is defined in-part by an endwall. The plug also defines a recess adapted to carry and retain a thermoluminescent dosimetry chip. When the plug is positioned in the recess defined by the frame, the end wall and the recess defined by the plug cooperate to form a chamber that encapsulates and protects the thermoluminescent dosimetry chip.

BRIEF DESCRIPTION OF THE DRAWINGS

FIG. 1 is an exploded view showing the housing, chip holder and thermoluminescent dosimetry chip of the present invention;

FIG. 2 is a perspective view of an eye protective device having the housing, thermoluminescent chip, and chip holder of FIG. 1, mounted thereon;

DETAILED DESCRIPTION OF THE PREFERRED EMBODIMENTS

Figure 3:
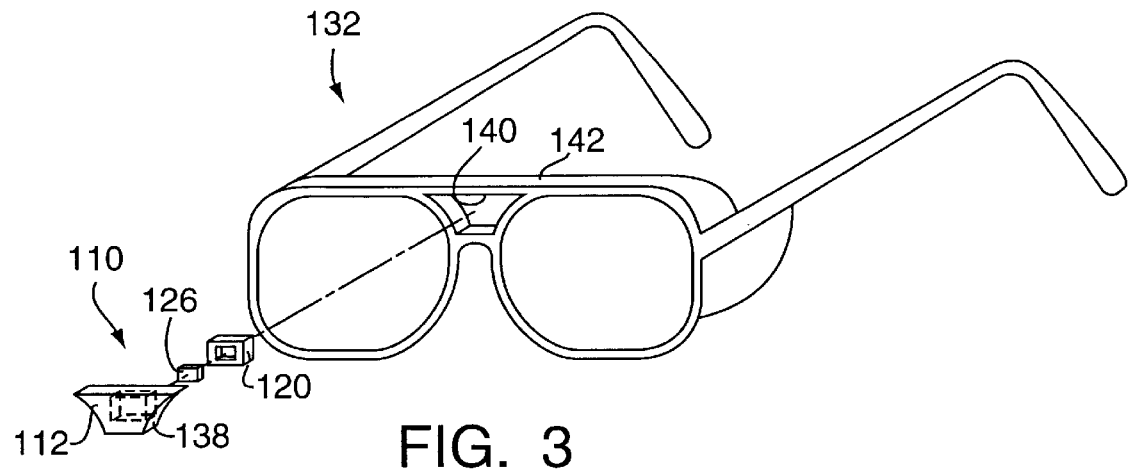
FIG. 3 is an exploded view of an eye protective device having a brow area that defines an opening, a housing receivable in the opening, and a chip holder and thermoluminescent dosimetry chip receivable in the housing.

An apparatus for measuring facial exposure to ionizing radiation, mountable on an eye protective device is shown in FIG. 1 and is generally designated by the reference numeral 10. The apparatus includes a housing 12 having a first recess 14 defined in-part by an end wall 16 as well as by an inner peripheral surface 18. A chip plug 20 is provided and defines an outer peripheral surface 22 of a shape complimentary to the inner peripheral surface 18 that defines the first recess 14. The plug 20 also defines a second recess 24 (shown in dotted lines) adapted to releasably receive and retain a thermoluminescent dosimetry (TLD) chip 26, preferably of the lithium fluoride type for measuring exposure to ionizing radiation.

Still referring to FIG. 1, once the TLD chip 26 is positioned in the second recess 24 defined by the plug 20, the plug is slidably positioned in the first recess 14 until it abuts the end wall 16. The end wall 16 and the second recess 24 cooperate to define a chamber (not shown) that encapsulates and protects the TLD chip 26 during use.

As shown in FIG. 2, an eye protective apparatus in the form of a pair of safety/eye glasses 28 includes at least one lens member 30 and a frame 32. The frame 32 includes a pair of ear pieces 34 and an elongated brow member 36 interposed between and attached to the ear pieces and extending across an upper portion of the lens member 30. The housing 12 having the plug 20 positioned in the first recess 14, and carrying the TLD chip 26 in the second recess 24 (not shown), is positioned between and frictionally retained by the brow member 36 and the lens member 30, with a portion of the brow member being received by a slot 38 extending longitudinally across and part-way through the housing.

A second embodiment of the apparatus of the present invention is shown in FIG. 3 and is generally designated by the reference numeral 110. The apparatus 110 is similar in many respects to the apparatus 10 described above, and therefore like reference numerals preceded by the number 1 are used to indicate like elements. The apparatus 110 differs from the apparatus 10 in that the holder 112 has an outer periphery 138 having a shape complimentary to an inner periphery 140 defined by an opening in an upper brow portion 142 of a frame 132. The plug 120 and the TLD chip 126 are positioned in the chip holder 112 in the same manner as described herein above.

In operation, the apparatus of the first and second embodiments, 10 and 110 respectively, are used in the same manner. The TLD chips, 26 and 126 are installed in their respective plugs 20 and 120, which in turn are installed in the housings 12 and 112. Subsequently, the housings 12 and 112 are installed in their respective frames 32 and 132. Accordingly, when a wearer places the eye protective device on his or her face; cumulative facial exposure to radiation will be measured by the TLD chip 26 or 126 over a predetermined monitoring period. When the period expires, the TLD chip 26 or 126 can then be removed from the plug 20 or 120 and processed to determine the extent of exposure.

Figure 4:
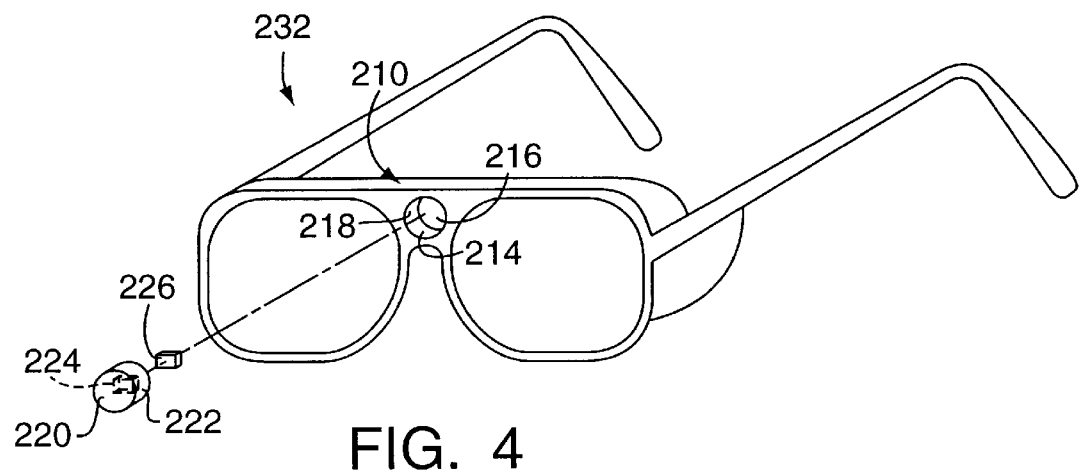
FIG. 4 is a perspective view of an eye protective device having a integral housing for receiving a thermoluminescent dosimetry chip carried by a chip holder.

A third embodiment of the apparatus of the present invention is shown in FIG. 4 and is generally designated by the reference numeral 210. The apparatus 210 is similar in many respects to the apparatus 10 described above, and therefore like reference numerals preceded by the number 2 are used to indicate like elements. The apparatus 210 differs from the apparatus 10 in that the holder 212 is an integral part of the frame 232 of the eye protective device. The chip holder 220 releasably retains a TLD chip 226, preferably of the lithium fluoride type, in the same manner as in the above-described embodiments. The holder 212 includes a first recess 214 defined by an end wall 216 and an inner peripheral surface 218. The chip holder 220 defines an outer peripheral surface 222 of a shape complimentary to the inner peripheral surface 218. Accordingly, once the TLD chip 226 is positioned in the second recess 224 (shown in dotted line), the plug 220 can be slidably positioned in the first recess 214 until it abuts the end wall 216. The end wall 216 and the second recess 224 cooperate to define a chamber (not shown) that encapsulates and protects the TLD chip 226.

In operation, the TLD chip 226 is installed in the chip holder 220 which in turn is slidably positioned in and frictionally retained by the first recess 214. When a wearer places the eye protective device on his or her face any facial exposure to ionizing radiation will be measured cumulatively by the TLD chip 226 over a predetermined monitoring period. When the monitoring period expires, the TLD chip 226 can be removed from the plug 220 and processed to determine exposure.

While preferred embodiments have been shown and described, various modifications and substitutions may be made without departing from the spirit and scope of the present invention. Accordingly, it is to be understood that the present invention has been described by way of example, and not by limitation.

What is claimed is:

1. An apparatus for measuring facial exposure to ionizing radiation, mountable on protective eyewear, comprising:

a housing including a first recess defined by an inner perimeter and an end wall;

a thermoluminescent dosimetry chip;

a plug having an outer perimeter of a shape complimentary to the inner perimeter, and defining a second recess adapted to receive and releasably retain the thermoluminescent dosimetry chip;

the plug carrying the thermoluminescent dosimetry chip being slidably received in and abutting the endwall of the first recess, the end wall and the second recess co-operating to define a chamber that encapsulates and protects the thermoluminescent dosimetry chip; and means for coupling the housing to an upper brow portion of the protective eyewear such that the thermoluminescent dosimetry chip is positioned between the eyes of the wearer and constitutes a self-contained radiation exposure measurement device thereby enabling the thermoluminescent dosimetry chip to measure the amount of ionizing radiation to which the face and eyes of the wearer are exposed.

2. An apparatus for measuring facial exposure to radiation as defined by claim 1, wherein:

the protective eyewear includes a frame having a bridge opening defined by a first inner perimeter; and wherein the means for coupling the housing to the protective eyewear includes a second outer perimeter defined by the housing and having a shape complimentary to the first inner perimeter for slidably receiving and frictionally retaining the housing in the bridge opening.

3. An apparatus for measuring facial exposure to radiation as defined by claim 1, wherein:

the protective eyewear is a pair of safety glasses having a frame releasably coupled to at least one lens member, and having a pair of ear pieces, an elongated brow member extending across an upper portion of the lens member, interposed between and coupled to the ear pieces; and wherein the means for coupling the housing to the safety glasses includes a slot defined by and extending part-way through the housing, the slot being adapted to receive a portion of the brow member when the housing is positioned between and frictionally retained by the lens and the brow members.

4. An apparatus for measuring facial exposure to radiation as defined by claim 1, wherein the thermoluminescent dosimetry chip is a lithium fluoride chip.

5. An apparatus for measuring facial exposure to radiation as defined by claim 1, wherein the housing is made from high density polypropylene.

6. An apparatus for measuring facial exposure to radiation as defined by claim 1, wherein the chip holder is made from high density polypropylene.

7. A pair of safety glasses having an integral radiation dosimeter, comprising:

a thermoluminescent dosimetry chip;

a frame including an upper brow area having a first recess defined by an inner perimeter and an end wall;

a plug including a second recess for releasably receiving and retaining the thermoluminescent dosimetry chip, the plug defining an outer perimeter of a shape complimentary to the inner perimeter, such that the plug can be slidably received in the first recess, with the end wall and the first recess cooperating to define a chamber that encapsulates and protects the dosimetry chip.

8. An apparatus for measuring facial exposure to radiation as defined by claim 7, wherein the thermoluminescent dosimetry chip is a lithium fluoride chip.

9. An apparatus for measuring facial exposure to radiation as defined by claim 7, wherein the chip holder is made from high density polypropylene.

\* \* \* \* \*